(12) United States Patent
Lamesic et al.

(10) Patent No.: US 10,568,837 B2
(45) Date of Patent: Feb. 25, 2020

(54) PARTICLES OF SPHERICALLY AGGLOMERATED LACTOSE FOR DIRECT COMPRESSION AND METHOD OF PREPARATION THEREOF

(71) Applicant: Dejan Lamesic, Velenje (SI)

(72) Inventors: Dejan Lamesic, Velenje (SI); Zoran Lavric, Zuzemberk (SI); Ilija Ilic, Ljubljana (SI); Odon Planinsek, Ljubljana (SI)

(73) Assignee: Dejan Lamesic (SI)

( * ) Notice: Subject to any disclaimer, the term of this patent is extended or adjusted under 35 U.S.C. 154(b) by 0 days.

(21) Appl. No.: 15/510,970

(22) PCT Filed: Sep. 10, 2015

(86) PCT No.: PCT/SI2015/000029
§ 371 (c)(1),
(2) Date: Mar. 13, 2017

(87) PCT Pub. No.: WO2016/039698
PCT Pub. Date: Mar. 17, 2016

(65) Prior Publication Data
US 2017/0239184 A1     Aug. 24, 2017

(30) Foreign Application Priority Data
Sep. 11, 2014   (SI) .................................. P-201400310

(51) Int. Cl.
*B32B 5/16* (2006.01)
*A61K 9/20* (2006.01)
(Continued)

(52) U.S. Cl.
CPC .......... *A61K 9/2018* (2013.01); *A61K 9/2077* (2013.01); *A61K 9/2095* (2013.01);
(Continued)

(58) Field of Classification Search
CPC .................................................... A61K 9/0075
(Continued)

(56) References Cited

FOREIGN PATENT DOCUMENTS

WO    WO-2004110585 A1 * 12/2004 ........... A61K 9/0075

OTHER PUBLICATIONS

Yang et al, L-Malic acid crystallization: polymorphism, semispherulites,twisting, and polarity, CrystEngComm, 2018, 20, 1383 (Year: 2018).*

(Continued)

*Primary Examiner* — Hoa (Holly) Le
(74) *Attorney, Agent, or Firm* — The Watson IP Group, PLC; Jovan N. Jovanovic

(57) ABSTRACT

Many active pharmaceutical ingredients are not directly compressible, therefore addition of pharmaceutical excipients is necessary. Fillers are essential pharmaceutical excipients, among which sugars are commonly employed, especially lactose. It is required that such substances have good flowability and compressibility. The present invention enables a simple and industry applicable production of particles of spherically agglomerated lactose that have suitable flow properties, excellent compression characteristics and reduce or prevent occurrence of segregation in mixture for production of solid dosage forms. They are porous spherical agglomerates. Particles of spherically agglomerated lactose comprise prism-like primary particles that are radially arranged and form a bigger agglomerate structure. Particles of spherically agglomerated lactose have suitable size, are highly breakable, have relatively high specific surface area and enable production of tablets with high tensile strength.

13 Claims, 5 Drawing Sheets

(51) Int. Cl.
    A61K 31/138    (2006.01)
    A61K 31/40     (2006.01)
    A61K 31/573    (2006.01)
(52) U.S. Cl.
    CPC ............ *A61K 31/138* (2013.01); *A61K 31/40* (2013.01); *A61K 31/573* (2013.01)
(58) Field of Classification Search
    USPC ........................................................ 428/402
    See application file for complete search history.

(56) References Cited

OTHER PUBLICATIONS

Nokhodchi et al: "Preparation of agglomerated crystals for improving flowability and compactibility of poorly flowable and compactible drugs and excipients", Powder Technology, vol. 175, No. 2, May 19, 2007, pp. 73-81.
Elsevier Sequoia, Lausanne, CH ISSN: 0032-5910, DOI: 10.1016/J.POWTEC.2007.01.030 the whole document.
Maghsoudi M et al: "Preparation of agglomerated crystals of lactose for direct tabletting by the spherical crystallization technique", Scientific Information Database Pharmaceutical Sciences, No. 4 2006, XP002752217, Retrieved from Internet: URL: http://en.journals.sid.ir/ViewPaper.aspx?ID=67767 Abstract.
Dr M C Gohel et al: "Corresponding Author: A review of co-processed directly compressible excipients" J Pharm Pharmaceut Sci (www.cspscanada.org), Jan. 1, 2005 (Jan. 1, 2005_, pp. 76-93 XP055109525, Retrieved from the Internet: URL: http://ualberta.ca/csps/JPPS8(1)/P.Jogani/excipients.pdf [retrieved on Mar. 24, 2014] the whole document.
Gokul R Ghenge et al: "An overview to spherical crystalisation and its evaluation", International Journal of Applied Pharmaceutics, Jan. 1, 2011 (Jan. 10, 2011), XP055235160, Retrieved from the Internet: URL: http://www/ijaponline.org/Vol3Issue3/145.pdf [retrieved on Dec. 9, 2015] the whole document.
Jyothi Thati et al., Particle engineering of benzoic acid by spherical agglomeration, 2012, p. 657-667, Europe.
Jyothi Katta et al., Spherical crystallization of benzoic acid, 2008, p. 61-69, Sweden.
Z.K Nagy et al., Modelling and control of combined cooling and antisolvent crystallization processes, 2008, p. 856-864, United Kingdom.
Marco Giulietti et al., Crystallization by Antisolvent Addition and Cooling, 2012, p. 379-397, Brazil.
Abhijit A. Lonare, Antisolvent Crystallization of Poorly Water Soluble Drugs, 2013, p. 337-341, India.
Kazuhiko Ikegami, Primary crystal growth during spherical agglomeration in liquid, 2002, p. 266-274, Japan.
Kazuhiko Ikegami, A new spherically agglomerated drug composite system with lactose for dry powder inhalation, 2003, p. 215-229, Japan.
Allan S. Myerson, Handbook of Industrial Crystallization, 2002, p. 219, 231, 246, 249, USA.
Wayne Genck, Make the Most of Antisolvent Crystallization, 2010, p. 1-7, USA.

* cited by examiner

PARTICLES OF SPHERICALLY AGGLOMERATED LACTOSE FOR DIRECT COMPRESSION AND METHOD OF PREPARATION THEREOF

TECHNICAL FIELD

The present invention relates to a spherical particle of lactose which can be used as a pharmaceutical excipient in production of solid dosage forms, especially those formed with direct compression. The presented particle of spherically agglomerated lactose is produced in the process of spherical agglomeration, where lactose solution is added to a nonsolvent. The said particle of spherically agglomerated lactose prepared according to the process of invention reduces or prevents occurrence of segregation in mixture of powders and enables production of tablets with increased tensile strength in comparison to the other commercially available lactose particles.

BACKGROUND ART

Solid dosage forms are preferential in pharmaceutical industry, especially tablets. To attain tablets of a sufficient quality pharmaceutical excipients which do not possess pharmacologic activity are used and are added to active pharmaceutical ingredient, in particular to enhance tableting properties that are essential for production of tablets.

Important group of pharmaceutical excipients are fillers, comprising different sugars, wherein lactose is the most extensively used in a pharmaceutical industry. In pharmaceutical processing is vital that said fillers demonstrate suitable properties, in particular good flowability and compressibility, especially with regard to tablets (Bolhuis K G, Armstrong A N. Excipients for direct compaction—un update. Pharmaceutical Development Technology 2006; 11: 111-124). Commercially accessible types of lactose for direct compression are prepared by different methods, therefore they possess different physicochemical properties with an intention to improve process difficulties with regard to poor flowability and/or compressibility. (Rowe R C, Sheskey P J, Quinn M R (Eds). Lactose, monohydrate in Handbook of Pharmaceutical Excipients 6th Ed., Pharmaceutical Press, 2009). Lactose is frequently produced with crystallization in the first stage, followed by milling and/or sieving in the second, respectively. The outcomes of the milling process are often particles with sharp edges, irregular form and small size that can have poor tableting properties, therefore are commonly subject of improvement. This is often achieved by procedures comprising: granulation, spray drying, physical modification of particles (dehydration, partial pregelatinization, etc.), co-processing, etc. (Bolhuis G K, Waard H. Compaction properties of directly compressible materials in Celik M (Ed). Pharmaceutical Powder Compaction Technology 2nd Ed., Informa Healthcare, 2011; Gohel M C. A review of co-processed directly compressible excipients. Journal of Pharmacological and Pharmaceutical Sciences 2005; 8: 76-93). Additional stages of manufacturing of lactose particles after crystallization are time consuming and less economical, therefore there is a substantial need for a plain, convenient and more economical process for a production of directly compressible lactose particles. Spherical crystallization, and more particularly, spherical agglomeration is considered as an adequate alternative technique to aforementioned methods.

Spherical agglomeration is a complex process, wherein crystallization of primary particles and agglomeration of said primary particles occur concurrently leading to formation of spherical agglomerates. Spherical agglomeration is only possible within maintained narrow crystallization conditions, therefore the parameters which lead to suitable conditions are difficult to discover. For effective spherical agglomeration process a plurality of, but not limited to, parameters are essential, such as composition of solvents, viscosity of a crystallization system, supersaturation of a solute solution, temperature of the crystallization system and stirring parameters that establish adequate hydrodynamic conditions. An appropriately guided process results in spherical agglomerates with adequate flow properties for tableting, high intrapartical porosity and brittleness that demonstrate great compressibility (Kovačič B, Vrečer F, Planinšek O. Spherical crystallization of drugs. Acta Pharmaceutica 2012; 62: 1-14).

The object of the present invention is to provide particles of spherically agglomerated lactose for direct compression with good flowability and compressibility produced in uniform process of spherical agglomeration without additional process stages (e.g. granulation, spray drying, etc.) required for improving flowabiltiy and compressibility.

Characteristics of particles are critical for adequate flow and compression properties of a tableting mixture in production of solid dosage forms like tablets. Flowability of a tableting mixture depends on particle size, its shape and morphology. Particles with smooth and round morphology with particle size larger than 100 µm are desired. Porosity of particles affects compression properties. The strength of tablets depends on number and potency of intraparticle and interparticle contact points that are formed during the production of dosage form, thus particles with large specific surface area and highly brittle particles are desired. Higher tablet strength prevents or minimizes very common tablet defects such as lamination and capping. Additionally, mechanical properties of tablets for handling and packaging are improved.

The simplest and most economical way of producing tablets is direct compression as it consists of two stages—blending of final tableting mixture and compression of said mixture into a tablet. Initial particles of which a tableting mixture is made of have often poor flowability and compressibility, therefore direct compression is not feasible. Hence, appropriate treatment of particles with granulation is necessary to obtain particles with good flowability and compressibility. Granulation is undesirable because specific equipment is necessary and many process stages are required to obtain tablets in comparison to direct compression.

Significant problem of a direct compression process is an occurrence of segregation or stratification of tableting mixture which has a significant influence on uniformity of content in a tablet and stability of the process itself. Segregation is commonly encountered during blending of tableting mixture, transport of tableting mixture, transfer of said mixture from blender to hopper and during tableting process because of elevated vibrations of tablet press, especially during higher tableting speeds. Segregation is mostly a consequence of difference in particle size, shape, density and adhesion forces among particles of different components in a tableting mixture. It can be limited by transformation of particles into granules but granulation is undesirable because specific equipment is necessary and many process stages are required to obtain tablets in comparison to direct compression. Segregation can be reduced or prevented by employing adequate excipient, therefore there is a substantial need for an excipient, with particles having porous structure and demonstrate suitable morphologic properties, like increased particle outer contact surface that prevents segregation.

Description of the Technical Problem

Many different types of lactose for direct compression are available on the market. They differentiate in particle size, shape, porosity, etc. (Gohel M C. A review of co-processed directly compressible excipients. Journal of Pharmacological and Pharmaceututical Sciences 2005; 8: 76-93; Miyamoto H. The particle design of cellulose and the other excipients for a directly compressible filler-binder. Kona Powder and Particle Journal 2008; 26: 142-152; Rowe R C, Sheskey P J, Quinn M R (Eds). Lactose, monohydrate in Handbook of Pharmaceutical Excipients 6th Ed., Pharmaceutical Press, 2009). Some types of lactose for direct compression possess good flowability but poor compressibility at the same time, or vice versa. Therefore, there is a substantial need for lactose particles which possess as many as possible favourable tableting properties, such as reduction or prevention of segregation and concurrently have good flowability and compressibility.

DETAILED DESCRIPTION OF PREFERRED EMBODIMENTS

Various objects, features, aspects and advantages of the present invention will become more apparent from the following detailed description of preferred embodiments of the invention along with the presented drawings.

PARTICLES

Figure 1:
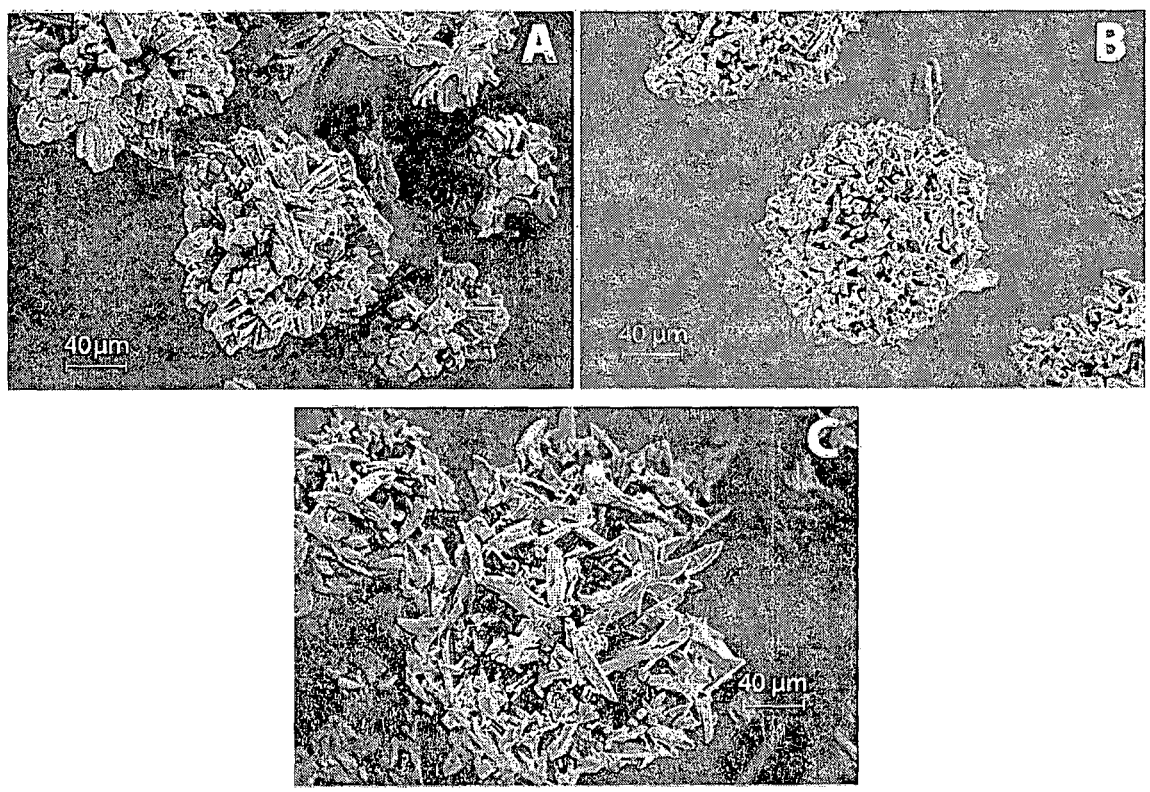
FIG. 1 is a scanning electron micrograph of an effect of temperature of crystallization medium on morphological properties of particles of spherically agglomerated lactose (A—Example 1, B—Example 2, C—Example 3).

The object of the present invention are particles of spherically agglomerated lactose for direct compression with favourable tableting properties produced in simple, economic and uniform process of spherical agglomeration. The first aspect of the present invention are porous particles of spherically agglomerated lactose with an average particle size of 50 to 1000 μm, more preferably of 75 to 500 μm and most preferably of 100 to 300 μm. Due to the production method of said particles of spherically agglomerated lactose, said particles demonstrate characteristic radial arrangement of prism-like primary particles, i.e. the primary particles are in a form of prism and/or in a form similar to prism, that form spherical agglomerate of lactose and furthermore enable improved tableting properties. Because of their typical structure particles of spherically agglomerated lactose possess high brittleness, are more prone to fragmentation upon compression and have higher specific surface area in comparison to commercially accessible types of lactose particles for direct compression. Another aspect of the present invention are particles of spherically agglomerated lactose with a specific surface area of 0.50 to 5.00 $m^2/g$, more preferably of 1.00 to 3.50 $m^2/g$ and most preferably of 1.25 to 2.50 $m^2/g$.

Particles of spherically agglomerated lactose of the present invention are highly compressible by means of more rapid reduction of porosity and volume, respectively. The result of a rapid reduction of volume and porosity are tablets of higher strength and higher tensile strength, respectively. It is not possible to determine the compressibility of lactose particles only due to the fact that the tablet produced of only lactose particles is not suitable for further handling and performing evaluation tests. For adequate measurement and determination of the compressibility additional pharmaceutical excipients have to be added. Hence, for determination of compressibility of tablets obtained from particles of spherically agglomerated lactose of the present invention the following tableting mixture composition was employed: 99.0 w/w % of particles of spherically agglomerated lactose of the invention and 1.0 w/w % of other pharmaceutical excipients. Compressibility was determined with modified out-die Walker analysis (Walker E E. The properties of powders VI: The compressibility of powders. Transactions of the Faraday Society 1923; 19:73-82; Sonnergaard J M. Quantification of the compactibility of pharmaceutical powders. European Journal of Pharmaceutics and Biopharmaceutics 2006; 63:270-277). The Walker coefficient for tableting mixture composed of particles of spherically agglomerated lactose of the invention is between 20.0 to 40.0% and more preferably between 26.0 to 35.0%.

Method of Preparation of Particles of Spherically Agglomerated Lactose

Lactose particles, intended for use as a pharmaceutical excipient are commonly formed with crystallization procedures, followed by milling and additional processing (e.g. spray drying, granulation, etc.) for improving flowability and/or compressibility of particles. Surprisingly and unexpectedly it has been found out that with a following method we can obtain lactose particles having good flowability and compressibility, without further processing requirement to improve these properties.

Another aspect of the present invention is a method of producing particles of spherically agglomerated lactose, said method comprising the following steps:

a) an adequate quantity of lactose is dissolved in a solvent in a concentration range (given as mass/mass concentration, which is a quotient of mass of lactose and mass of a solution multiplied with one hundred in percent unit) from 0.1% to 75.0%, more preferably from 7.5%0 to 55.0% and most preferably from 17.5% to 35.0%. Temperature of so prepared lactose solution is regulated in the range from −10° C. to 90° C., more preferably from 25° C. to 65° C. and most preferably from 35° C. to 50° C.;

b) temperature of a nonsolvent is regulated in the range from −20° C. to 115° C., more preferably from 5° C. to 50° C. and most preferably from 5° C. to 20° C.;

c) lactose solution from step a) is added to a nonsolvent at a certain flow rate and at maintained stirring and temperature of the crystallization medium as defined in step b). Crystallization medium may be optionally further stirred for a preferable amount of time after the addition of lactose solution to a nonsolvent;

d) so obtained final product, which is precipitated lactose is separated from a suspension and is dried at temperature from 20° C. to 130° C., more preferably from 30° C. to 60° C. and most preferably from 40° C. to 50° C.

Lactose used to obtain lactose solution may be present in a solid state in any isomer form (α-lactose monohydrate, anhydrous lactose and β-lactose) or in a combination of two or more isomer forms in all ratios. Nonsolvent in the present invention may be any alcohol, but not limited to, selected from a group comprising methanol, ethanol, n-propanol, 2-propanol, n-butanol. More preferable nonsolvent is 2-propanol and most preferable ethanol. Nonsolvent may also be a mixture of selected alcohols and/or a mixture of water and selected alcohol and/or mixtures of several selected alcohols and water, wherein the mass ratio of alcohol in resulted mixture of water and alcohol/alcohols is higher than 50% and more preferably higher than 70%.

Solvent in the present invention may be water and/or mixture of water and alcohol, wherein alcohol in the mixture is one or more alcohols, but not limited to, selected from a group comprising methanol, ethanol, n-propanol, 2-propanol, n-butanol, wherein the mass ratio of a selected alcohol/alcohols in the resulted mixture of water and alcohol/alcohols is lower than 30% and more preferable lower than 10%.

Those skilled in the art will appreciate that a separation of the final product, i.e. particles of spherically agglomerated lactose may be achieved by any means of separation, preferably with filtration. Drying of separated humid lactose particles may be achieved with any known technique for drying.

Use

Another aspect of the present invention is the use of particles of spherically agglomerated lactose in powder mixtures for direct compression comprising at least one active pharmaceutical ingredient and optionally other pharmaceutical excipients usually used in production of tablets. Capping and lamination of a tablet is a common defect obtained during tableting. Those skilled in art usually avoid this defect by producing tablets with higher strength or higher tensile strength. Particles of spherically agglomerated lactose according to the invention enable production of tablets of higher strength or higher tensile strength upon compression with relatively lower force than tablets obtained from commercially available types of lactose.

The determination of tensile strength of tablets produced from lactose particles only is not possible because the produced tablet does not attain suitable properties for performing required tests; therefore the addition of other suitable pharmaceutical excipients is necessary. For determination of a tablet tensile strength, a tableting mixture composed of 99.0 w/w % of particles of spherically agglomerated lactose of the present invention and 1.0 w/w % of other pharmaceutical excipients is employed. Tablets produced from particles of spherically agglomerated lactose presented in this invention upon compression pressure of 130 MPa have tensile strength from 0.8 to 3.5 MPa, more preferably from 1.2 to 2.7 MPa and most preferably from 1.4 to 2.0 MPa.

Another aspect of the present invention is the use of particles of spherically agglomerated lactose for reduction or prevention of segregation that can be encountered during blending of tableting mixture, transport of tableting mixture, transfer of said mixture from blender to hopper and during tableting process because of elevated vibrations of tablet press. Particles of spherically agglomerated lactose prepared by the disclosed method has porous structure and favourable morphologic properties, like increased particle outer contact surface that enable mechanical entrapment of particles of active pharmaceutical ingredient between primary particles of spherical agglomerate. Proportion of the adhered active pharmaceutical ingredient onto the particles of spherically agglomerated lactose is increased by this way, resulting in improved homogeneity of mixture for production of solid dosage forms and thus effectively reduces or prevents segregation in comparison to other commercially available types of lactose.

Methods

Average particle size was determined with the laser diffraction method (e.g. Mastersizer S, Malvern, Great Britain) by dispersion of lactose particles in 96 v/v % ethanol.

Specific surface area of spherical agglomerates of lactose was determined with adsorption BET (Brunauer, Emmett, Teller) analysis (TriStar 3000, Micromeritics, USA; nitrogen gas used).

Tensile strength was determined with compression of tableting mixture with the following composition: 99.0 w/w % particles of spherically agglomerated lactose according to the invention or commercially available types of lactose particles, 0.5 w/w % binder copovidone (Kollidon® VA 64, BASF, Germany) and 0.5 w/w % anti-adhesive magnesium stearate (Ligastar MG 700, Peter Greven, Germany). Those skilled in the art will appreciate that tableting mixture was prepared by known procedures, wherein preceding sieving for removal of larger particles was employed followed by addition of individual components of tableting mixture and mixing of tableting mixture to obtain proper homogeneity. Tablets with a mass 400 mg were compressed with a single punch tablet press (Kilian SP300, IMA Kilian, Germany) with a flat round punch of the diameter 12.0 mm and compression pressure range from 50 to 220 MPa. 24 hours after compression of tablets the strength of tablets was measured (Vanderkamp VK 200) and the tensile strength of tablets compressed at 130 MPa was calculated (Fell J T, Newton J M. Determination of tablet strength by the diametral compression test. Journal of Pharmaceutical Sciences 1970; 59:688-691).

For the same tableting mixtures made in the same way as defined above the compressibility was determined by an out-die Walker analysis. 24 hours after compression, the tablets mass and size were determined. From obtained data the Walker profile was designed. Walker profile demonstrates dependence of a specific volume with regard to the compression pressure. With a linear regression a slope of a linear part of a curve (compression pressure in range from 40 to 160 MPa) is determined that represents Walker coefficient (w').

The present invention will be described in more detail with the reference to the examples. Those skilled in art will appreciate that many modifications with regard to the substance and procedures may be performed without departing from the inventive concepts described herein.

EXAMPLES

Example 1

50 g of lactose is dissolved in 220 ml of purified water at elevated temperature. The solution of lactose is then regulated at 40° C. 500 ml of ethanol-water mixture (96 v/v % ethanol) is regulated at temperature of 5° C. Aqueous lactose solution is added to ethanol-water mixture at a flow rate of 4.7 ml/min under constant stirring conditions of 350 revolutions per minute with a 4-bladed mechanical stirrer. Crystallization system is regulated at constant temperature of 5° C. After the addition of aqueous lactose solution stirring is continued for additional 15 minutes at the temperature of crystallization system 5° C. Formed suspension is vacuum filtrated and dried in a laboratory drier for 12 hours at 40° C.

Example 2

Particles in Example 2 are prepared by the same procedure as described in Example 1, except that the initial ethanol-water mixture (96 v/v % ethanol) and the crystallization system are regulated at temperature of 10° C.

Example 3

Particles in Example 3 are prepared by the same procedure as described in Example 1, except that the initial ethanol-water mixture (96 v/v % ethanol) and the crystallization system are regulated at temperature of 20° C.

Average particle size of dried particles prepared by Example 1-3 was measured with a laser diffraction method and is shown in Table 1.

TABLE 1

Influence of temperature of spherical agglomeration on average particle size.

| Example | Temperature [° C.] | Average particle size [μm] |
|---------|-------------------|----------------------------|
| 1 | 5 | 172.6 |
| 2 | 10 | 186.5 |
| 3 | 20 | 189.0 |

The morphology of particles prepared by Example 1-3 was examined using scanning electron microscope. Particle morphology is shown in FIG. 1.

As seen in Table 1, the temperature of the ethanol-water mixture and further crystallization system does not have significant impact on particle size. Morphology of prepared particles is similar in all examples. Particles are porous spherical agglomerates composed of many primary particles (e.g. prisms, needles, etc.) arranged radially outwards from the centre of the particle and form a bigger agglomerate structure. Particles prepared in Example 2 demonstrate the best tableting properties with regard to flowability and compressibility.

Example 4

75 g of lactose is dissolved in 220 ml of purified water at high temperature. The solution of lactose is then regulated at 40° C. 500 ml of ethanol-water mixture (96 v/v % ethanol) is regulated at temperature of 10° C. Aqueous lactose solution is added to ethanol-water mixture at a flow rate of 4.7 ml/min under constant stirring conditions of 350 revolutions per minute with a 4-bladed mechanical stirrer. Crystallization system is regulated at constant temperature of 10° C. After the addition of aqueous lactose solution, stirring is continued for additional 15 minutes at the temperature of crystallization system 10° C. Formed suspension is vacuum filtrated and dried in a laboratory drier for 12 hours at 40° C.

Example 5

Particles in Example 5 are prepared by the same procedure as described in Example 4, except that 100 g of lactose was dissolved in 220 ml of purified water at high temperature.

Average particle size of dried particles prepared by Example 2, 4 and 5 was measured with a laser diffraction method and is shown in Table 2.

TABLE 2

Influence of initial aqueous lactose concentration on average particle size.

| Example | w/w % lactose concentration | Average particle size [μm] |
|---------|-----------------------------|----------------------------|
| 2 | 18.5 | 186.5 |
| 4 | 25.4 | 208.6 |
| 5 | 31.3 | 215.6 |

Figure 2:
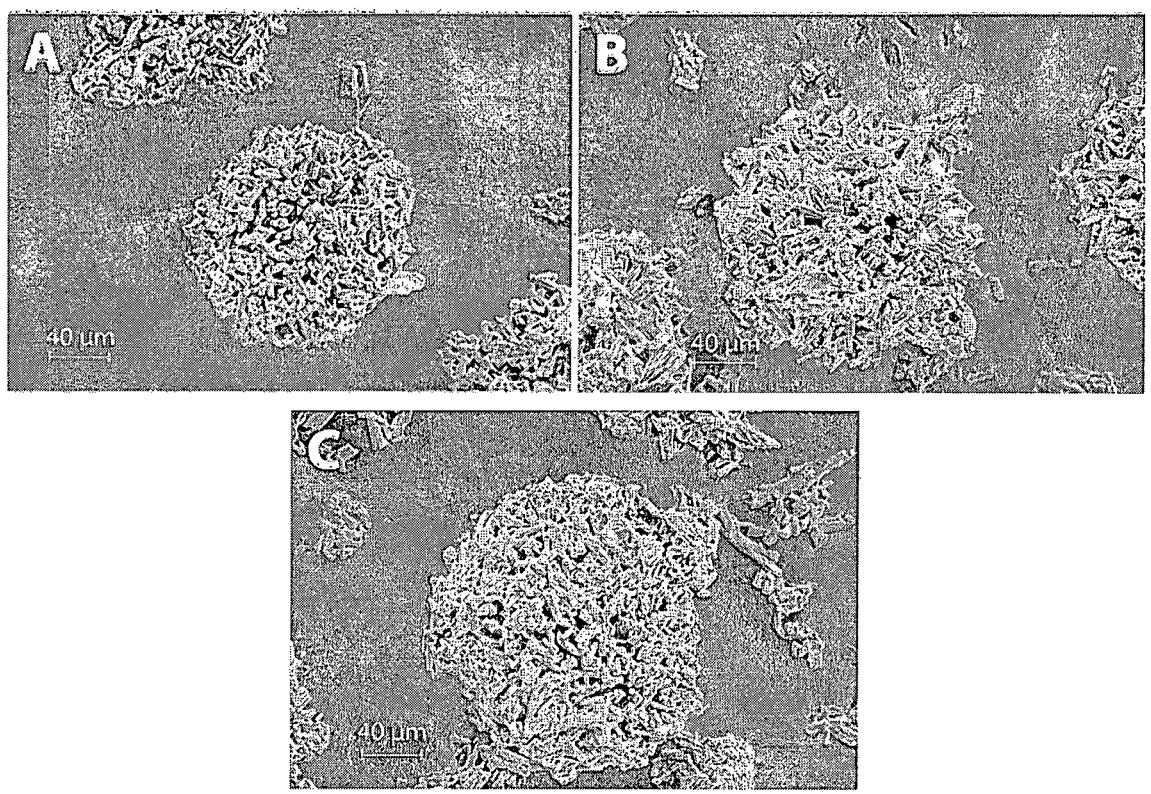
FIG. 2 is a scanning electron micrograph of an effect of initial aqueous lactose concentration on morphological properties of particles of spherically agglomerated lactose (A—Example 2, B—Example 4, C—Example 5).

The morphology of particles prepared by Example 2, 4 and 5 was examined using scanning electron microscope. Particle morphology is shown in FIG. 2.

As seen in Table 2, the initial aqueous lactose concentration has an impact on an average particle size. Lower initial aqueous lactose concentration yields smaller spherical agglomerates in comparison to higher initial aqueous lactose concentration, while morphology of all particles prepared in Example 2, 4 and 5 is still adequate.

Example 6

50 g of lactose is dissolved in 220 ml of purified water at high temperature. The solution of lactose is then regulated at 40° C. 500 ml of ethanol-water mixture (96 v/v % ethanol) is regulated at temperature of 10° C. Aqueous lactose solution is added to ethanol-water mixture at a flow rate of 4.7 ml/min under constant stirring conditions of 250 revolutions per minute with a 4-bladed mechanical stirrer. Crystallization system is regulated at constant temperature of 10° C. After the addition of aqueous lactose solution, stirring is continued for additional 15 minutes at the crystallization system temperature of 10° C. Formed suspension is vacuum filtrated and dried in a laboratory drier for 12 hours at 40° C.

Figure 3:
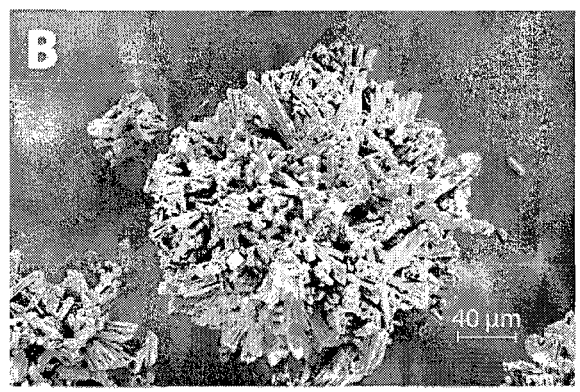
FIG. 3 is a scanning electron micrograph of morphological properties of the particle of spherically agglomerated lactose prepared by Example 6.

Average particle size of dried particles prepared by Example 6 was measured with a laser diffraction method and morphology of particles was examined by scanning electron microscope. Particle morphology is shown in FIG. 3.

Average size of particles prepared by Example 6 is 241.6 μm. Moreover, it is demonstrated that different stirring velocity provides particles with adequate size and adequate morphologic properties.

Example 7

50 g of lactose is dissolved in 220 ml of purified water at high temperature. The solution of lactose is then regulated at 40° C. 500 ml of ethanol-water mixture (96 v/v % ethanol) is regulated at temperature of 10° C. Aqueous lactose solution is added to ethanol-water mixture at a flow rate of 4.7 ml/min under constant stirring conditions of 350 revolutions per minute with a 4-bladed mechanical stirrer. Crystallization system is regulated at constant temperature of 10° C. After the addition of aqueous lactose solution, stirring is continued for additional 30 minutes at the crystallization system temperature of 10° C. Formed suspension is vacuum filtrated and dried in a laboratory drier for 12 hours at 40° C.

Example 8

Example 8 depicts direct compression of a tableting mixture, comprising particles of spherically agglomerated lactose prepared in Example 7 and illustrates some important technical characteristics of spherical agglomerates in comparison to commercially available particles of lactose. Reference lactose particles are commercially available lactose particles used as fillers for direct compression. Particles of spherically agglomerated lactose according to the invention were compared to following reference lactose particles: Tablettose® 70 (Meggle, Germany), Tablettose® 80 (Meggle, Germany), Lactopress® SD250 (DFE Pharma, Germany), SuperTab® 11SD (DFE Pharma, Germany) in SuperTab' 14SD (DFE Pharma, Germany). Tablettose® particles are agglomerates of primary particles produced in a granulation process, while Lactopress® and SuperTab® particles are obtained by spray drying process.

Tableting mixtures were prepared with the following composition: 99.0 w/w % particles of spherically agglomerated lactose according to the invention or commercially available types of lactose particles, 0.5 w/w % binder copovidone (Kollidon® VA 64, BASF, Germany) and 0.5 w/w % anti-adhesive magnesium stearate (Ligastar MG 700, Peter Greven, Germany). Those skilled in the art will appreciate that tableting mixtures were prepared by known procedures, wherein preceding sieving for removal of larger particles was employed, followed by addition of individual components of tableting mixture and mixing of tableting mixture to obtain proper homogeneity. Tablets with a mass of 400 mg were compressed with a single punch tablet press (Kilian SP300, IMA Kilian, Germany) with a flat round punch of a diameter 12.0 mm and compression force range from 50 to 220 MPa. 24 hours after compression of tableting mixtures the strength of tablets was measured (Vanderkamp VK 200) and the tensile strength of tablets compressed at 130 MPa was calculated (Fell J T, Newton J M. Determination of tablet strength by the diametral compression test. Journal of Pharmaceutical Sciences 1970; 59:688-691). Tableting mixtures of the examples are named after lactose, of which they are prepared.

For the same tableting mixtures made in the same way as defined above the compressibility was determined by an out-die Walker analysis. 24 hours after compression, the tablets mass and size were determined. From obtained data the Walker profile was designed. Walker profile demonstrates dependence of a specific volume with regard to the compression pressure. With a linear regression a slope of linear part of a curve (compression pressure from 40 to 160 MPa) is determined that represents Walker coefficient (absolute slope multiplied with one hundred; w').

Figure 4:
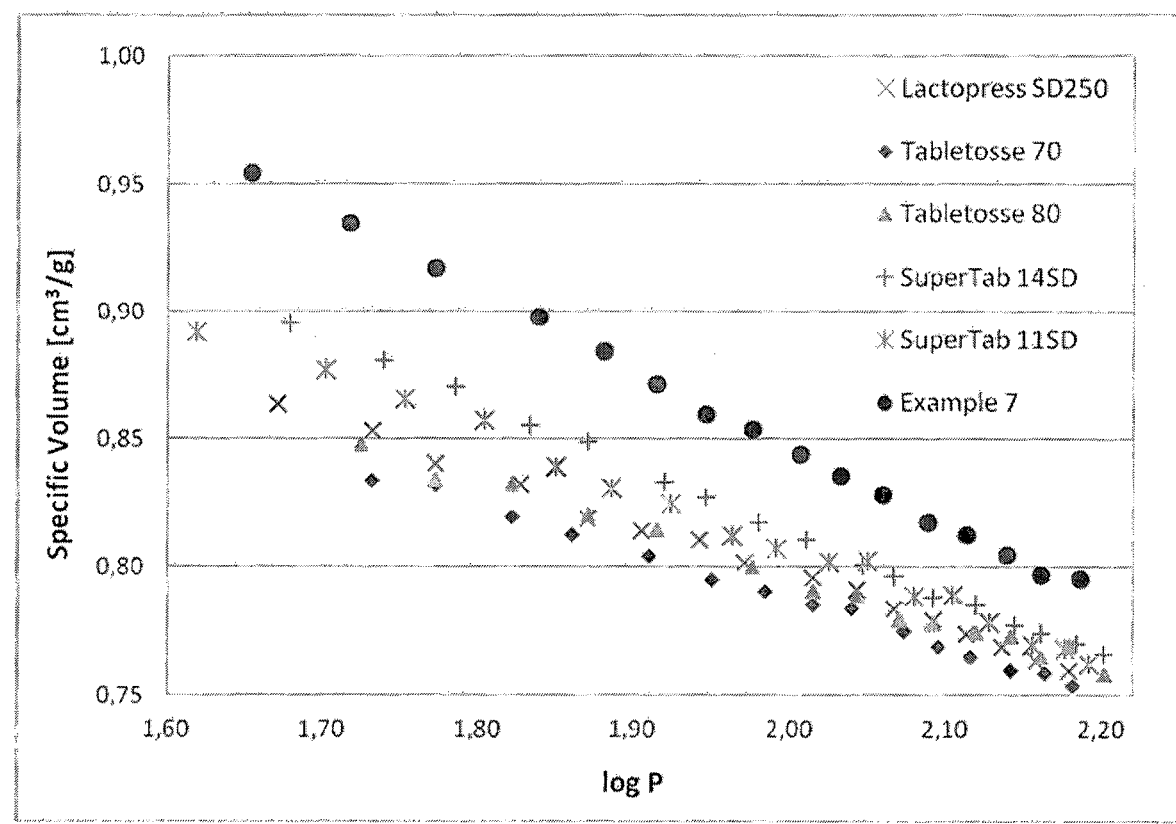
FIG. 4 is a graph showing the comparison of Walker profiles of reference lactose particles and particles of spherically agglomerated lactose prepared by example 7.

FIG. 4 represents graph of so obtained Walker profiles of selected tableting mixtures. Specific volume of tableting mixture prepared from particles of spherically agglomerated lactose obtained by Example 7 is significantly higher in comparison to the reference tableting mixtures, composed of commercially available lactose particles. Significantly higher specific volume of tableting mixture prepared from particles of spherically agglomerated lactose obtained by Example 7 may be due to higher intraparticle porosity, as is clearly observed from scanning electron microscope photos, while interparticle porosity is similar among all tableting mixtures. Furthermore, particles of spherically agglomerated lactose prepared by Example 7 are increasingly more compressible as the specific volume is reduced more rapidly compared to the reference lactose particles which is demonstrated in significantly steeper slope and greater Walker coefficient (w, Table 3).

Figure 5:
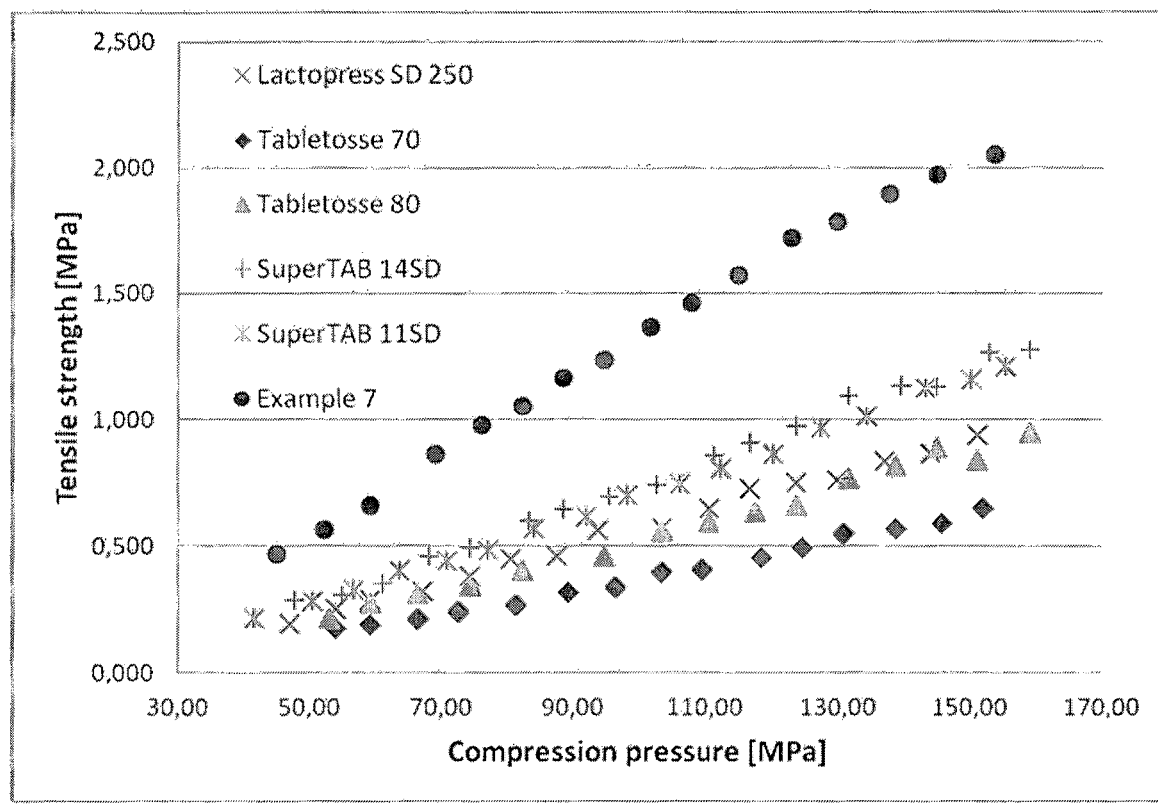
FIG. 5 is a graph showing the comparison of compactibility profiles of reference lactose particles and particles of spherically agglomerated lactose prepared by example 7.

Compression characteristics can be characterized with a compactibility profile, as shown on FIG. 5. It demonstrates that particles of spherically agglomerated lactose have greater compactibility in comparison to the reference lactose particles. Tensile strength of tablets made out of tableting mixture composed of particles of spherically agglomerated lactose by Example 7 is significantly higher within all pressure range compared to the reference lactose particles. Higher tensile strength prevents very common tablet defects like capping and lamination, and at the same time provides increased mechanical resistance necessary for further tablet handling and packaging. Values of tensile strength measured at compression pressure 130 MPa are presented in Table 3.

TABLE 3

Results of Walker and compactibility analysis of selected lactose particles.

| Tableting mixture | $P_1 - P_2$ [MPa] | $R^2$ | w' [%] | Tensile strength at 130 MPa [MPa] |
|---|---|---|---|---|
| Lactopress ® SD 250 | 47-160 | 0.9961 | 19.91 | 0.788 |
| Tablettose ® 70 | 54-161 | 0.9957 | 18.05 | 0.526 |
| Tablettose ® 80 | 53-159 | 0.9910 | 18.29 | 0.734 |
| SuperTab ® 11SD | 42-156 | 0.9942 | 22.72 | 0.975 |
| SuperTab ® 14SD | 40-159 | 0.9989 | 25.18 | 1.027 |
| Example 7 | 45-161 | 0.9986 | 30.57 | 1.767 |

$P_1 - P_2$ pressure range employed in Walker analysis
$R^2$ coefficient of determination of linear regression within the pressure range $P_1 - P_2$ Compression properties of selected tableting mixtures are presented in Table 3 in the form of Walker coefficient and tensile strength at compression pressure of 130 MPa. Particles of spherically agglomerated lactose prepared by Example 7 have superior compression properties compared to the reference lactose particles, defined with higher compressibility as well as higher compactibility (higher tensile strength). They show much desired qualities with regard to compression properties of particles. Particles of spherically agglomerated lactose according to the invention are highly porous and because of their characteristic radial structure are more brittle and highly breakable, hence the number of contact points between particles upon compression is increased which increases tensile strength of tablets.

Average particle size and BET specific surface area of reference (spray dried and agglomerated) lactose particles that gave highest tensile strength of tablets and particles of spherically agglomerated lactose obtained by Example 7 were measured. Results are shown in Table 4.

TABLE 4

Average particle size and BET specific surface area of selected samples.

| Lactose | Average particle size [µm] | BET [m²/g] |
|---|---|---|
| Example 7 | 244.6 | 1.66 |
| SuperTab ® 14SD | 117.7 | 0.57 |
| Tablettose ® 70 | 218.8 | 1.17 |

Particles of spherically agglomerated lactose obtained by Example 7 have significantly higher specific surface area compared to reference lactose particles. This represents one of the essential characteristics of particles of lactose according to the invention and is attributed to their characteristic internal structure. Particle of spherically agglomerated lactose is composed of many prism-like primary particles which are radially organised in a characteristic structure that significantly increase specific surface area compared to the reference lactose particles.

Example 9

Example 9 presents the use of particles of spherically agglomerated lactose prepared by Example 7.

TABLE 5

Tablet formulation by Example 9.

| Substance | Mass of substance per tablet |
| --- | --- |
| Atorvastatin | 10.00 |
| Lactose (by Example 7) | 100.00 |
| Microcrystalline cellulose | 30.00 |
| Polyvinylpyrrolidone | 5.00 |
| Croscarmellose sodium | 4.00 |
| Magnesium stearate | 0.50 |

Atorvastatin, lactose, microcrystalline cellulose, polyvinylpyrrolidone and croscarmellose sodium are sieved through sieve 500 µm, weighted and homogenously mixed. Magnesium stearate is added and obtained powder mixture additionally mixed for 5 minutes. Tableting mixture is compressed into tablets with a theoretical mass of 149.5 mg.

Example 10

Example 10 presents the use of spherical agglomerates of lactose prepared by Example 7.

TABLE 6

Tablet formulation by Example 10.

| Substance | Mass of substance per tablet (mg) |
| --- | --- |
| Fluoxetine | 10.00 |
| Lactose (by Example 7) | 86.80 |
| Microcrystalline cellulose | 15.00 |
| Sodium starch glycolate | 4.00 |
| Magnesium stearate | 0.50 |

Fluoxetine, lactose, microcrystalline cellulose and sodium starch glycolate are sieved through sieve 250 µm, weighted and homogenously mixed. Magnesium stearate is added and obtained powder mixture additionally mixed for 5 minutes. Tableting mixture is compressed into tablets with a theoretical mass of 116.3 mg. Tablets may be optionally coated to assure prolonged release.

Example 11

Example 11 presents the use of spherical agglomerates of lactose prepared by Example 7.

TABLE 7

Tablet formulation by Example 11.

| Substance | Mass of substance per tablet (mg) |
| --- | --- |
| Prednisolone | 20.00 |
| Lactose (for granulation) | 50.20 |
| Lactose (by Example 7) | 106.30 |
| Microcrystalline cellulose | 58.50 |
| Corn starch | 30.00 |
| Sodium starch glycolate | 9.00 |
| Silicon dioxide | 1.00 |
| Magnesium stearate | 2.00 |

Prednisolone, 50.2 g of lactose for granulation, microcrystalline cellulose and corn starch are sieved through sieve 500 µm, weighted and placed into a high-shear mixer. Granulation is achieved with water addition. Wet granules are sieved and dried. Silicon dioxide, sodium starch glycolate and lactose (by Example 7) are extragranularly added to dried granules and mixed homogenously. In so obtained powder mixture magnesium stearate is added and again mixed homogenously. Tableting mixture is compressed into tablets with a theoretical mass of 277.0 mg.

Example 12

Example 12 presents the comparison between the proportion of adherence of a model substance tartrazine onto the particles of spherically agglomerated lactose obtained by Example 7 and the proportion of adherence onto the reference commercially available lactose particles for direct compression. Particles of spherically agglomerated lactose obtained by Example 7 were compared to Tablettose® 70 (Meggle, Germany) and Flowlac® 100 (Meggle, Germany).

Particle size fraction of lactose higher than 125 µm and particle size fraction of tartrazine below 63 µm were obtained by means of sieving. Binary mixtures of tartrazine and individual lactose were prepared in mass ratio 1:15. Mixtures were blended in laboratory type mixer (Bioengineering Inversina) for 20 minutes with 90 revolutions per minute. Prepared mixtures were exposed to a mechanical stress that simulates conditions during tableting process which can lead to segregation. Prepared mixtures were sieved for 10 minutes (sive size 100 µm) on an agitation plate (Retsch AS 200) with an amplitude 1 mm. Remaining fraction on the sieve were spectrophotometrically analysed to obtain proportion of adhered tartrazine on lactose (Table 8).

TABLE 8

Proportion of adhered model substance tartrazine on lactose particles

| Lactose | Proportion of tartrazine [%] |
| --- | --- |
| Lactose (by Example 7) | 2.09 |
| Flowlac ® 100 | 0.56 |
| Tablettose ® 70 | 1.37 |

Particles of spherically agglomerated lactose obtained by Example 7 capture significantly higher proportion of tartrazine in comparison to the reference lactose particles. Mechanical capture into intraparticle pores reduces or prevents segregation that may be a consequence of elevated vibrations of tablet press during tableting.

Example 13

Transferring of tableting blend between hoppers causes a formation of cone like pile upon powder flow. Particles arrange differently considering their flow properties. Particles with better flow properties slide further on a formed pile, contrary to particles which possess worse flow properties. Example 13 presents results of evaluating segregation in binary mixtures of particles of spherically agglomerated lactose obtained by Example 7 with an active pharmaceutical ingredient carvedilol compared to the results of two reference lactose types: Tablettose® 70 (Meggle, Germany) and Flowlac® 100 (Meggle, Germany).

Particle size fraction of lactose higher than 125 µm and particle size fraction of carvedilol below 63 µm were obtained by means of sieving. Mixtures of carvedilol and individual lactose were prepared with a mass ratio of carvedilol 15% and 25%. Mixtures were blended in laboratory type mixer (Bioengineering Inversina) for 20 minutes with 90 revolutions per minute. Individual binary mixture was poured into a glass funnel for measuring flow time. Flow of particles through the funnel created cone like structure. Cone piles were sampled on four symmetric locations on a circumference and one at the top. The content of carvedilol was determined spectrophotometrically and relative standard deviation of content was calculated (Table 9 and Table 10).

TABLE 9

Relative Standard deviation of carvedilol content in binary mixture of an individual lactose and carvedilol (15% of carvedilol in mixture) after flow through a glass funnel.

| Lactose | RSD [%] |
|---|---|
| Lactose (by Example 7) | 2.75 |
| Flowlac ® 100 | 6.41 |
| Tablettose ® 70 | 6.83 |

TABLE 10

Relative standard deviation of carvedilol content in binary mixture of an individual lactose and carvedilol (25% of carvedilol in mixture) after flow through a glass funnel.

| Lactose | RSD [%] |
|---|---|
| Lactose (by Example 7) | 4.87 |
| Flowlac ® 100 | 11.04 |
| Tablettose ® 70 | 10.33 |

Particles of spherically agglomerated lactose obtained by the Example 7 form significantly more homogenous mixture compared to the reference types of lactose as the relative standard deviation was the lowest. Mechanical entrapment of carvedilol into the intrapartical pores of spherical agglomerates according to the invention and increased outer contact surface reduces or prevents occurrence of segregation that can be a consequence of difference in size, shape and density of particles during the transport of tableting mixture from a mixer to a hopper.

The invention claimed is:

1. Particles of spherically agglomerated lactose for reduction or prevention of segregation and for direct compression, comprising:
    an agglomerate center; and
    primary particles surrounding the agglomerate center, the primary particles being prism-shaped and radially arranged outward and surrounding the agglomerate center.

2. The particles of spherically agglomerated lactose according to claim 1, wherein the average particle size is from 50 to 1000 μm and specific surface area of the particles is from 0.50 to 5.00 $m^2/g$.

3. The particles of spherically agglomerated lactose according to claim 1, wherein the particles have high compressibility, wherein the compressibility is determined with Walker coefficient for a tableting mixture and is from 20.0 to 40.0%, wherein the tableting mixture consists of at least 99% w/w of particles of spherically agglomerated lactose.

4. The particles of spherically agglomerated lactose according to claim 1, wherein the particles have high tensile strength, wherein the tensile strength upon compression pressure of 130 MPa is from 0.8 to 3.5 MPa, wherein the tensile strength is determined by compression of tableting mixture consisting of at least 99% w/w of particles of spherically agglomerated lactose.

5. A process for a production of particles of spherically agglomerated lactose, comprising the following steps:
    a) a first step of preparation of lactose solution by dissolving lactose in a solvent, wherein the solvent is water;
    b) a second step of addition of said lactose solution to a nonsolvent, the nonsolvent being an alcohol, wherein the particles of spherically agglomerated lactose precipitate; and
    c) a third step of separation of precipitated particles of spherically agglomerated lactose comprising an agglomerate center and primary particles surrounding the agglomerate center, the primary particles being prism-shaped and radially arranged outward and surrounding the agglomerate center, from a suspension and drying.

6. The process according to claim 5, wherein the lactose is in any isomer form or combination of two or more forms in any ratio and that the concentration of lactose solution is from 0.1% to 75.0%, given as weight-weight concentration, and the temperature of lactose solution is from −10° C. to 90° C.

7. The process according to claim 5, wherein the solvent further includes a mixture of the alcohol, wherein the alcohol in the mixture is one or more alcohols selected from a group comprising methanol, ethanol, n-propanol, 2-propanol, n-butanol, and the mass ratio of a selected alcohol/alcohols in the resulted mixture of water and alcohol/alcohols is lower than 30%.

8. The process according to claim 5, wherein the nonsolvent further includes the water, wherein the alcohol is selected from a group comprising methanol, ethanol, n-propanol, 2-propanol and n-butanol and a mass ratio of alcohol or alcohols in a mixture with water is higher than 50% and a temperature of a nonsolvent is from −20° C. to 115° C.

9. The process according to claim 8, wherein the nonsolvent is ethanol.

10. Particles of spherically agglomerated lactose prepared by the process according to claim 5.

11. The process according to claim 5, further comprising producing dosage forms with direct compression including the particles of spherically agglomerated lactose.

12. The process according to claim 5, further comprising reducing or preventing segregation in powder mixtures including the particles of spherically agglomerated lactose.

13. The process according to claim 5, wherein the addition of said lactose solution to the nonsolvent occurs at constant stirring.

* * * * *